(12) United States Patent
Wuttke et al.

(10) Patent No.: US 7,571,722 B2
(45) Date of Patent: Aug. 11, 2009

(54) NEBULIZER

(75) Inventors: Gilbert Wuttke, Dortmund (DE); Hubert Kunze, Dortmund (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 221 days.

(21) Appl. No.: 11/466,954

(22) Filed: Aug. 24, 2006

(65) Prior Publication Data

US 2007/0062519 A1    Mar. 22, 2007

Related U.S. Application Data

(63) Continuation-in-part of application No. 11/064,614, filed on Feb. 24, 2005, now abandoned, and a continuation of application No. PCT/EP2005/001947, filed on Feb. 24, 2005.

(30) Foreign Application Priority Data

Feb. 24, 2004   (DE) ................. 20 2004 002 610
Jul. 29, 2004    (DE) ................. 10 2004 036 925

(51) Int. Cl.
   *A61M 11/00*   (2006.01)
   *A61M 15/00*   (2006.01)
   *A61M 16/00*   (2006.01)
(52) U.S. Cl. .................... 128/200.14; 128/203.12; 128/203.15
(58) Field of Classification Search ............ 128/200.14, 128/200.16, 200.18, 200.21, 200.22, 202.22, 128/203.27, 204.23, 204.26, 203.23, 203.24; 222/190, 211; 239/327, 343
See application file for complete search history.

(56) References Cited

U.S. PATENT DOCUMENTS

| | | | |
|---|---|---|---|
| 2,535,844 | A | 12/1950 | Emerson |
| 2,882,026 | A | 4/1959 | Eichelman |
| 3,467,092 | A | 9/1969 | Bird et al. |
| 3,580,249 | A | 5/1971 | Takaoka |
| 3,584,621 | A | 6/1971 | Bird et al. |
| 3,630,196 | A | 12/1971 | Bird et al. |
| 3,658,059 | A | 4/1972 | Steil |
| 3,826,255 | A | 7/1974 | Havstad et al. |
| 3,838,686 | A | 10/1974 | Szekely |
| 3,874,379 | A | 4/1975 | Enfield et al. |
| 3,990,442 | A | 11/1976 | Patneau |

(Continued)

FOREIGN PATENT DOCUMENTS

DE    199 02 844 C1    11/1999

(Continued)

OTHER PUBLICATIONS

U.S. Appl. No. 10/101,554, filed Mar. 19, 2002 and entitled "Nebulizer Apparatus and Method".

(Continued)

*Primary Examiner*—Justine R Yu
*Assistant Examiner*—Annette F Dixon
(74) *Attorney, Agent, or Firm*—David S. Safran; Roberts Mlotkowski Safran & Cole, P.C.

(57) ABSTRACT

A nebulizer for a fluid, particularly for medicinal aerosol therapy. To allow easy operation, the nebulizer has a valve device, so that air supply openings in a mouthpiece can be blocked off to prevent backflow.

27 Claims, 13 Drawing Sheets

U.S. PATENT DOCUMENTS

| Patent | | Date | Inventor | Ref |
|---|---|---|---|---|
| 4,094,317 | A * | 6/1978 | Wasnich | 128/200.16 |
| 4,106,503 | A | 8/1978 | Rosenthal et al. | |
| 4,113,809 | A * | 9/1978 | Abair et al. | 261/81 |
| 4,116,387 | A | 9/1978 | Kremer, Jr. et al. | |
| 4,150,071 | A | 4/1979 | Pecina | |
| 4,198,969 | A | 4/1980 | Virag | |
| 4,251,033 | A | 2/1981 | Rich et al. | |
| 4,268,460 | A | 5/1981 | Boiarski et al. | |
| 4,333,450 | A | 6/1982 | Lester | |
| 4,413,784 | A | 11/1983 | Dea | |
| 4,456,016 | A | 6/1984 | Nowacki et al. | |
| 4,470,412 | A | 9/1984 | Nowacki et al. | |
| 4,588,129 | A | 5/1986 | Shanks | |
| 4,620,670 | A | 11/1986 | Hughes | |
| 4,674,491 | A | 6/1987 | Brugger et al. | |
| 4,677,975 | A | 7/1987 | Edgar et al. | |
| 4,746,067 | A | 5/1988 | Svoboda | |
| 4,758,224 | A | 7/1988 | Siposs | |
| 4,792,097 | A | 12/1988 | Kremer, Jr. et al. | |
| 4,796,614 | A | 1/1989 | Nowacki et al. | |
| 4,803,977 | A * | 2/1989 | Kremer, Jr. | 600/3 |
| 4,809,692 | A | 3/1989 | Nowacki et al. | |
| 4,832,015 | A | 5/1989 | Nowacki et al. | |
| 4,984,158 | A | 1/1991 | Hillsman | |
| 5,020,530 | A | 6/1991 | Miller | |
| 5,054,477 | A | 10/1991 | Terada et al. | |
| 5,054,478 | A | 10/1991 | Grychowski et al. | |
| 5,086,765 | A | 2/1992 | Levine | |
| 5,165,392 | A | 11/1992 | Small | |
| 5,167,506 | A | 12/1992 | Kilis et al. | |
| 5,170,782 | A | 12/1992 | Kocinski | |
| 5,241,954 | A | 9/1993 | Glenn | |
| 5,277,175 | A | 1/1994 | Riggs et al. | |
| 5,280,784 | A | 1/1994 | Kohler | |
| 5,284,133 | A | 2/1994 | Burns et al. | |
| 5,299,565 | A | 4/1994 | Brown | |
| 5,301,662 | A | 4/1994 | Bagwell et al. | |
| 5,301,663 | A | 4/1994 | Small, Jr. | |
| 5,309,900 | A | 5/1994 | Knoch et al. | |
| 5,312,046 | A | 5/1994 | Knoch et al. | |
| 5,318,015 | A | 6/1994 | Mansson et al. | |
| 5,363,842 | A | 11/1994 | Mishelevich et al. | |
| 5,385,140 | A | 1/1995 | Smith | |
| 5,398,714 | A | 3/1995 | Price | |
| 5,408,994 | A | 4/1995 | Wass et al. | |
| 5,435,282 | A * | 7/1995 | Haber et al. | 128/200.16 |
| 5,458,136 | A | 10/1995 | Jaser et al. | |
| 5,479,920 | A | 1/1996 | Piper et al. | |
| 5,487,378 | A | 1/1996 | Robertson et al. | |
| 5,505,192 | A | 4/1996 | Samiotes et al. | |
| 5,505,193 | A | 4/1996 | Ballini et al. | |
| 5,511,538 | A | 4/1996 | Haber et al. | |
| 5,515,842 | A | 5/1996 | Ramseyer et al. | |
| 5,520,166 | A | 5/1996 | Ritson et al. | |
| 5,533,497 | A | 7/1996 | Ryder | |
| 5,533,501 | A | 7/1996 | Denyer | |
| 5,549,102 | A | 8/1996 | Lintl et al. | |
| 5,570,682 | A | 11/1996 | Johnson | |
| 5,584,285 | A | 12/1996 | Salter et al. | |
| 5,613,489 | A | 3/1997 | Miller et al. | |
| 5,617,844 | A | 4/1997 | King | |
| 5,622,162 | A | 4/1997 | Johansson et al. | |
| 5,630,409 | A | 5/1997 | Bono et al. | |
| 5,687,912 | A | 11/1997 | Denyer | |
| 5,738,087 | A | 4/1998 | King | |
| 5,792,057 | A | 8/1998 | Rubsamen et al. | |
| 5,803,078 | A | 9/1998 | Brauner | |
| 5,823,179 | A | 10/1998 | Grychowski et al. | |
| 5,833,088 | A | 11/1998 | Kladders et al. | |
| 5,875,774 | A | 3/1999 | Clementi et al. | |
| 5,881,718 | A | 3/1999 | Mortensen et al. | |
| 6,044,841 | A | 4/2000 | Verdun et al. | |
| 6,098,618 | A | 8/2000 | Jennings et al. | |
| 6,116,233 | A | 9/2000 | Denyer et al. | |
| 6,129,080 | A | 10/2000 | Pitcher et al. | |
| 6,131,568 | A | 10/2000 | Denyer et al. | |
| 6,158,428 | A * | 12/2000 | Mecikalski | 128/200.23 |
| 6,176,237 | B1 * | 1/2001 | Wunderlich et al. | 128/203.12 |
| 6,223,745 | B1 | 5/2001 | Hammarlund et al. | |
| 6,234,167 | B1 * | 5/2001 | Cox et al. | 128/200.14 |
| 6,237,589 | B1 * | 5/2001 | Denyer et al. | 128/200.21 |
| 6,450,163 | B1 | 9/2002 | Blacker et al. | |
| 6,513,519 | B2 | 2/2003 | Gallem | |
| 6,543,448 | B1 | 4/2003 | Smith et al. | |
| 6,550,477 | B1 | 4/2003 | Casper et al. | |
| 6,581,596 | B1 | 6/2003 | Truitt et al. | |
| 6,584,976 | B2 | 7/2003 | Japuntich et al. | |
| 6,606,990 | B2 | 8/2003 | Stapleton et al. | |
| 6,612,303 | B1 | 9/2003 | Grychowski et al. | |
| 6,640,805 | B2 | 11/2003 | Castro et al. | |
| 6,644,304 | B2 | 11/2003 | Grychowski et al. | |
| 6,669,176 | B2 | 12/2003 | Rock | |
| 6,698,421 | B2 | 3/2004 | Attolini | |
| 6,729,328 | B2 | 5/2004 | Goldemann | |
| 6,732,731 | B1 | 5/2004 | Tseng | |
| 6,779,520 | B2 | 8/2004 | Genova et al. | |
| 6,823,862 | B2 | 11/2004 | McNaughton | |
| 6,848,443 | B2 * | 2/2005 | Schmidt et al. | 128/200.23 |
| 6,904,908 | B2 * | 6/2005 | Bruce et al. | 128/200.23 |
| 6,994,083 | B2 | 2/2006 | Foley et al. | |
| 7,131,440 | B2 * | 11/2006 | Sonntag | 128/203.12 |
| 7,131,441 | B1 | 11/2006 | Keller et al. | |
| 2002/0020762 | A1 | 2/2002 | Selzer et al. | |
| 2002/0157663 | A1 | 10/2002 | Blacker et al. | |
| 2003/0005929 | A1 | 1/2003 | Grychowski et al. | |
| 2003/0015193 | A1 | 1/2003 | Grychowski et al. | |
| 2003/0136499 | A1 | 7/2003 | Foley et al. | |
| 2004/0010239 | A1 | 1/2004 | Hochrainer et al. | |
| 2004/0134494 | A1 | 7/2004 | Papania et al. | |
| 2004/0231667 | A1 | 11/2004 | Horton et al. | |
| 2005/0028815 | A1 | 2/2005 | Deaton et al. | |

FOREIGN PATENT DOCUMENTS

| | | |
|---|---|---|
| DE | 199 02 847 C1 | 5/2000 |
| EP | 0 414 536 A2 | 2/1991 |
| EP | 0 587 380 B1 | 3/1993 |
| EP | 0587380 | 3/1994 |
| EP | 0 641 570 A1 | 3/1995 |
| EP | 0 711 609 A3 | 10/1996 |
| EP | 0 855 224 A2 | 7/1998 |
| EP | 0 938 906 A2 | 9/1999 |
| EP | 1 245 244 A2 | 10/2002 |
| FR | 1 070 292 | 7/1954 |
| GB | 675524 | 7/1952 |
| GB | 2 347 870 A | 9/2000 |
| WO | WO 88/03419 A | 5/1988 |
| WO | WO 91/14468 A1 | 10/1991 |
| WO | WO 97/12687 A1 | 4/1997 |

OTHER PUBLICATIONS

International Search Report for PCT/IB 02/05524 dated May 20, 2003.

Photographs of nebulizer manufactured by PARI GmbH with detachable gas flow interrupter believed to have been publicly available prior to Feb. 13, 1996.

PARI LC Plus Instructions for Use (GB), PARI GmbH, dated Jul. 2001.

* cited by examiner

NEBULIZER

CROSS-REFERENCE TO RELATED APPLICATION

This application is a continuation-in-part of U.S. patent application Ser. No. 11/064,614 and a continuation of International Patent Application PCT/EP05/001947 which designated the United States.

BACKGROUND OF THE INVENTION

1. Field of the Invention

The present invention relates to a nebulizer for a fluid with a mouthpiece and at least one air supply opening associated with the mouthpiece, the fluid being sprayable into the mouthpiece and to a mouthpiece for a nebulizer or other inhaler.

2. Description of Related Art

The starting point for the present invention is a nebulizer in the form of an inhaler sold under the trademark RESPIMAT®, which is illustrated in its basic structure in International Patent Application Publication WO 91/14468 A1 (corresponding U.S. Pat. Nos. 5,497,944 and 5,662,271) and in a specific embodiment in FIGS. 6a, 6b of International Patent Application Publication WO 97/12687 A1 (corresponding U.S. Pat. Nos. 6,726,124 and 6,918,547) and in FIGS. 1 and 2 of the accompanying drawings of this application. The nebulizer has, as a reservoir for fluid which is to be atomized, an insertable rigid container with an inner bag containing the fluid and a pressure generator with a drive spring for delivering and atomizing the fluid.

To supplement the disclosure of the present application reference is made to the complete disclosure of both WO 91/14468 A1 and WO 97/12687 A1 and their U.S. Patent counterparts indicated above. Generally, the disclosure contained therein preferably relates to a nebulizer with a spring pressure of 5 to 200 MPa, preferably 10 to 100 MPa on the fluid, with a volume of fluid delivered per stroke of 10 to 50 µl, preferably 10 to 20 µl, most preferably about 15 µl. The fluid is converted into an aerosol, the droplets of which have an aerodynamic diameter of up to 20 µm, preferably 3 to 10 µm. Furthermore, the disclosure contained therein preferably relates to a nebulizer of cylindrical shape of about 9 cm to about 15 cm and about 2 cm to about 5 cm wide and with a jet spray angle of 20° to 160°, preferably 80° to 100°. These values also apply to the nebulizer according to the teaching of the present invention as particularly preferred values.

By rotating an actuating member in the form of a lower housing part of the nebulizer, the drive spring can be put under tension and fluid can be drawn up into a pressure chamber of the pressure generator. After manual actuation of a locking element, the fluid in the pressure chamber is put under pressure by the drive spring and expelled through a nozzle into a mouthpiece to form an aerosol, without the use of propellant gas or the like. The speed of the aerosol cloud is very low, with the result that the cloud of aerosol is virtually stationary in the mouthpiece. A user then has to inhale the resulting aerosol slowly for as long as possible, e.g., 10 seconds or more. The mouthpiece has at least one air supply opening through which the user, on inhaling, sucks in air from the atmosphere together with the aerosol produced. This ensures that the air stream of supplied air and aerosol necessary for inhalation is produced and that the volume of aerosol needed for the inhalation process is available.

SUMMARY OF THE INVENTION

An object of the present invention is to provide a nebulizer and a mouthpiece with improved safety of operation, so that it is ensured that the aerosol can be breathed in or inhaled safely even when a user has problems coordinating the operation of the nebulizer with their breathing in.

The above object is achieved by a nebulizer in which the air supply opening or air supply openings is or are associated with at least one valve device by means of which a backflow through the air supply opening or openings can be blocked and by a mouthpiece having a chemical or an air supply opening for supplying ambient air, in order to generate an air current with sufficient volume for breathing in or inhaling, and with a valve device by which backflow through the channel or the air supply opening can be blocked.

A basic idea of the present invention resides in the fact that the nebulizer or the mouthpiece comprises a valve device which is associated with the air supply opening or openings, so that backflow—i.e., blow-out—through the air supply opening or openings can be prevented. Thus, an inexpensive and effective method is provided to ensure that breathing out by the user does not result in an unwanted expulsion of the nebulized fluid or aerosol from the mouthpiece through the air supply opening or openings into the environment.

The valve device provided preferably ensures that, in the event of the user (unintentionally) breathing out into the mouthpiece, an overpressure is produced which indicates a malfunction to the user, to inform him that in future he should only breathe out when using the nebulizer.

Moreover, after the user has accidentally breathed out prematurely, inhalation can be continued, as the nebulized fluid or aerosol still present in the mouthpiece can continue to be breathed in.

The solution described is applicable not only to the RESPIMAT® nebulizer or inhaler described above, but also to any kind of inhaler in which an aerosol produced has to be supplied with air from the atmosphere through a mouthpiece having air supply openings to achieve the inhalation volume needed for the user. Preferably, the invention is used in RESPIMAT® type nebulizers. In addition to the preferred RESPIMAT®, described in detail above, in particular, it is also possible to use nebulizers in which propellant-free aqueous or alcoholic solutions containing active substances are nebulized. However, the invention may also be used in conventional propellant-driven nebulizers or inhalers, particularly so-called MDIs (metered dose inhalers) and other nebulizers.

According to a particularly preferred feature, the valve device has an associated sensor for detecting opening or closing or movement of a valve element of the valve device. Thus, correct use of the nebulizer, e.g., sufficiently long and/or powerful inhalation, can be detected. The nebulizer preferably comprises a suitable monitoring device or the like.

Further advantages, features, properties and aspects of the present invention will become apparent from the following description of preferred embodiments referring to the drawings.

DETAILED DESCRIPTION OF THE INVENTION

Figure 1:
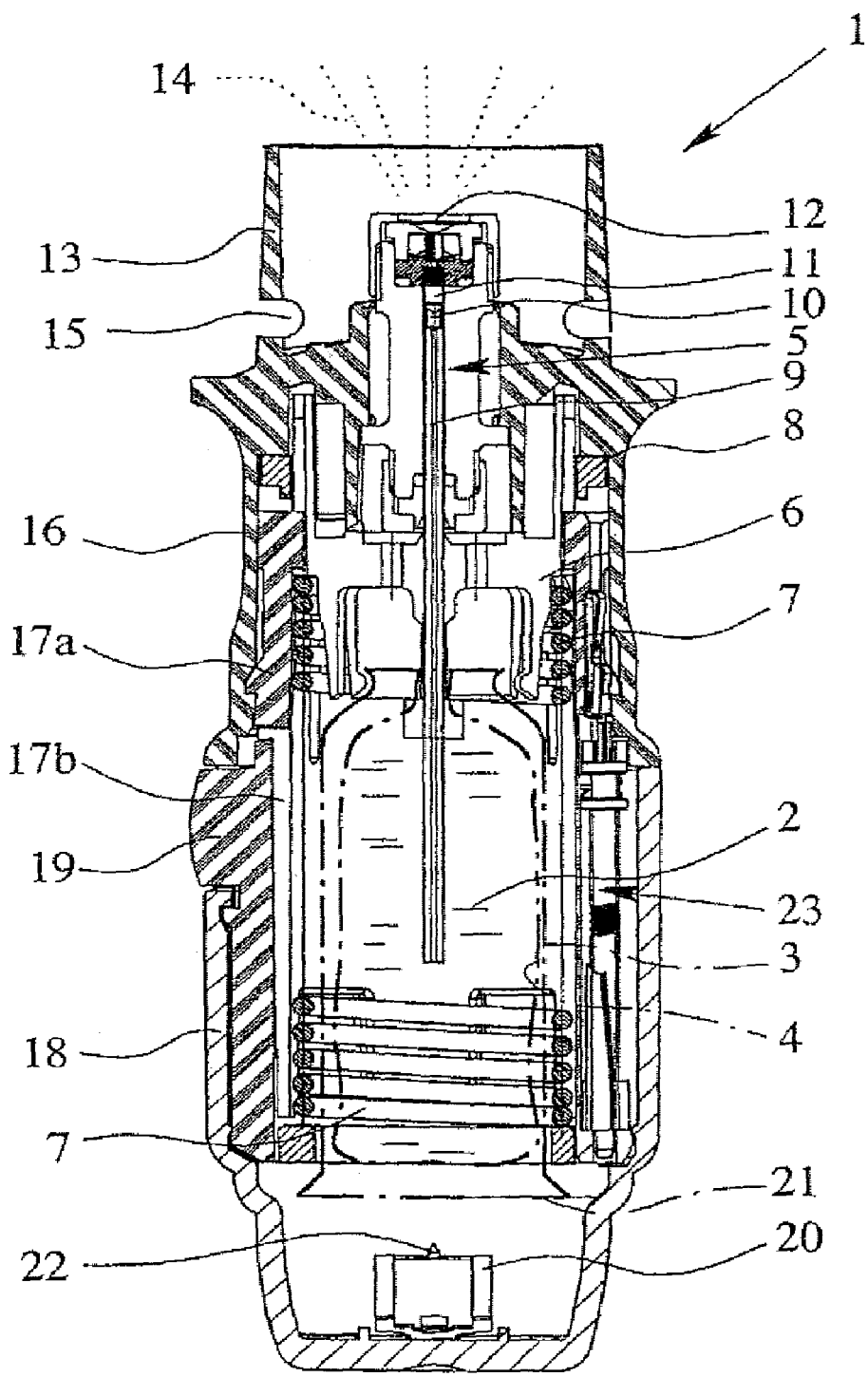
FIG. 1 is a diagrammatic section through a known nebulizer in the untensioned state.

In the figures, identical reference numerals are used for identical or similar parts, and corresponding or comparable properties and advantages are achieved even if the description is not repeated.

Figure 2:
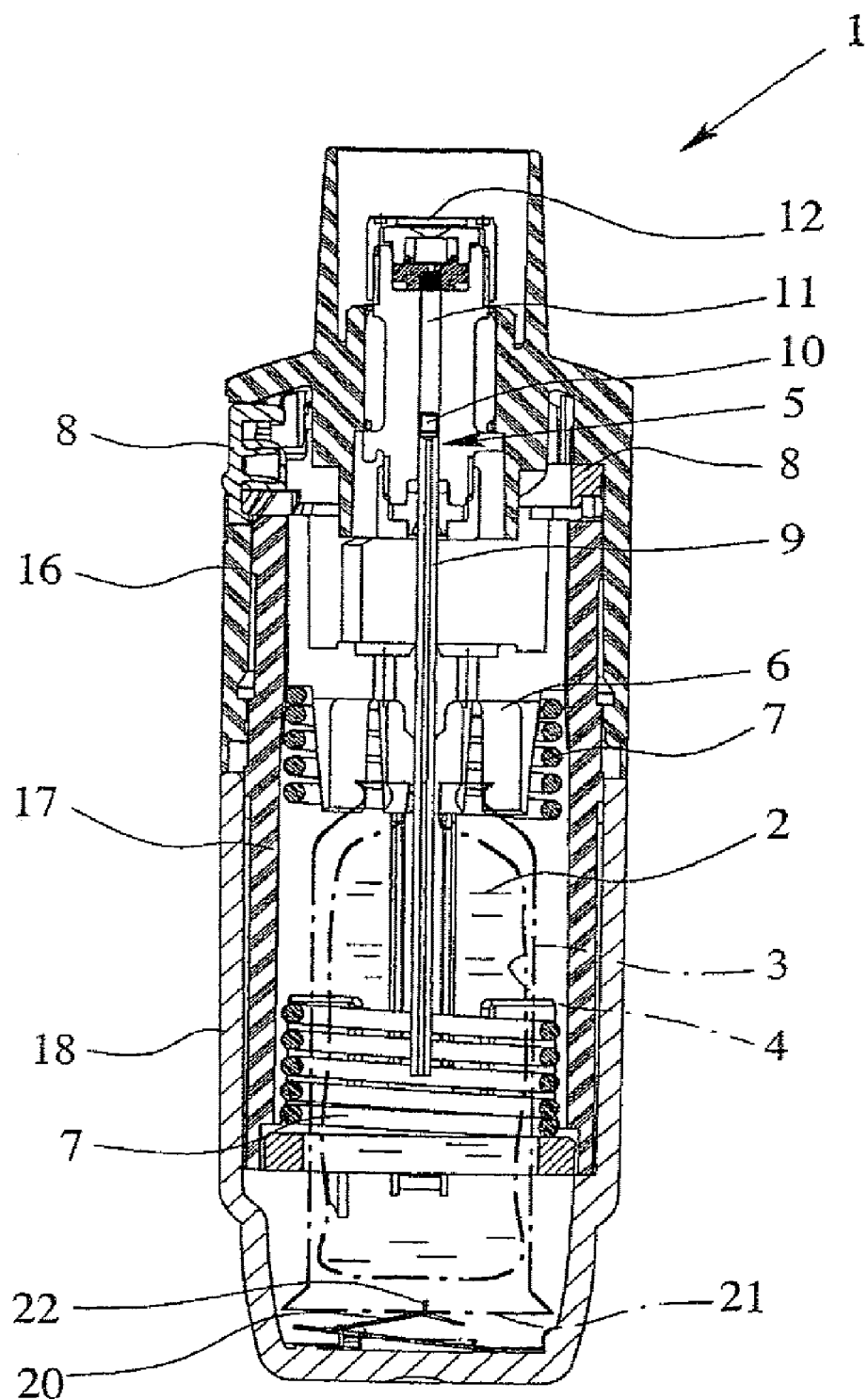
FIG. 2 shows a diagrammatic section through the known nebulizer in the tensioned state, rotated through 90° as compared with FIG. 1.

FIGS. 1 & 2 show a known nebulizer 1 for nebulizing a fluid 2, particularly a highly effective pharmaceutical composition or the like, viewed diagrammatically in the untensioned state (FIG. 1) and in the tensioned state (FIG. 2). The nebulizer is constructed, in particular, as a portable inhaler and preferably operates without propellant gas.

When the fluid 2, preferably a liquid, more particularly a pharmaceutical composition, is nebulized, an aerosol is formed which can be breathed in or inhaled by a user (not shown). Usually, the inhaling is done at least once a day, more particularly, several times a day, preferably at set intervals.

The nebulizer 1 has an insertable and preferably exchangeable container 3 containing the fluid 2, which forms a reservoir for the fluid 2 which is to be nebulized. Preferably, the container 3 contains an amount of fluid 2 which contains sufficient amounts of active substance formulations to provide, for example, up to 100 dosage units. A typical container 3, as disclosed in WO 96/06011 A1 and corresponding U.S. Pat. No. 5,833,088, holds a volume of about 2 to 10 ml.

The container 3 is substantially cylindrical or cartridge-shaped and once the nebulizer 1 has been opened, the container can be inserted therein from below and changed if desired. It is preferably of rigid construction, the fluid 2, in particular, being held in a collapsible bag 4 in the container 3.

The nebulizer 1 has a pressure generator 5 for conveying and nebulizing the fluid 2, particularly in a preset and optionally adjustable dosage amount. The pressure generator 5 has a holder 6 for the container 3, an associated drive spring 7, shown only in part, with a locking element 8 which can be manually operated to release it, a conveying tube 9 with a non-return valve 10, a pressure chamber 11 and an expulsion nozzle 12 in the region of a mouthpiece 13. The container 3 is fixed in the nebulizer 1 by means of the holder 6 such that the conveying tube 9 is immersed in the container 3. The holder 6 may be constructed so that the container 3 can be changed.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10. As the expulsion nozzle 12 has a very small cross section of flow and is constructed, in particular, as a capillary, such a strong throttle action is produced that the intake of air by suction is reliably prevented at this point even without a non-return valve.

During the subsequent relaxation after actuation of the locking element 8, the fluid 2 in the pressure chamber 11 is put under pressure as the conveying tube 9 with its non-return valve 10 now closed is moved back upwards by the relaxation of the drive spring 7 and now acts as a pressure ram. This pressure forces the fluid 2 through the expulsion nozzle 12, where it is nebulized into an aerosol 14. The droplet size of the particles for a RESPIMAT® type nebulizer has already been described above.

A user (not shown) can inhale the aerosol 14, while an air supply can be sucked into the mouthpiece 13 through at least one air supply opening 15.

The nebulizer 1 comprises an upper housing part 16 and an inner part 17 which is rotatable relative thereto, having an upper part 17a and a lower part 17b, while a housing part 18 which is, in particular, manually operable, is releasably fixed, particularly fitted, onto the inner part 17, preferably by means of a retaining element 19. In order to insert and/or replace the container 3 the housing part 18 can be detached from the nebulizer 1.

The housing part 18 can be rotated counter to the housing part 16, taking with it the part 17b of the inner part 17 which is the lower part in the drawings. In this way, the drive spring 7 is tensioned in the axial direction by means of a gear (not shown) acting on the holder 6. During tensioning, the container 3 is moved axially downwards until the container 3 assumes an end position as shown in FIG. 2. In this position, the drive spring 7 is under tension. During the nebulizing process, the container 3 is moved back into its original position by the drive spring 7. The container 3 thus performs a stroke during the tensioning process and during nebulization.

The housing part 18 preferably forms a cap-like lower housing part and fits around or over a lower free end portion of the container 3. As the drive spring 7 is tensioned, the container 3 moves with its end portion (further) into the housing part 18 or towards the end face thereof, while an axially acting spring 20 arranged in the housing part 18 comes to bear on the base 21 of the container and pierces the container 3 or a seal on its base with a piercing element 22 when the container makes contact with it for the first time, to allow air in.

The nebulizer 1 comprises a monitoring device 23 which counts the actuations of the nebulizer 1, preferably by detecting any rotation of the inner part 17 relative to the upper housing part 16.

The construction and mode of operation of a proposed nebulizer 1 will now be described in more detail, referring to FIGS. 3 to 22, but emphasizing only the essential differences from the nebulizer 1 according to FIGS. 1 & 2. The remarks relating to FIGS. 1 & 2 thus apply accordingly.

Figure 3:
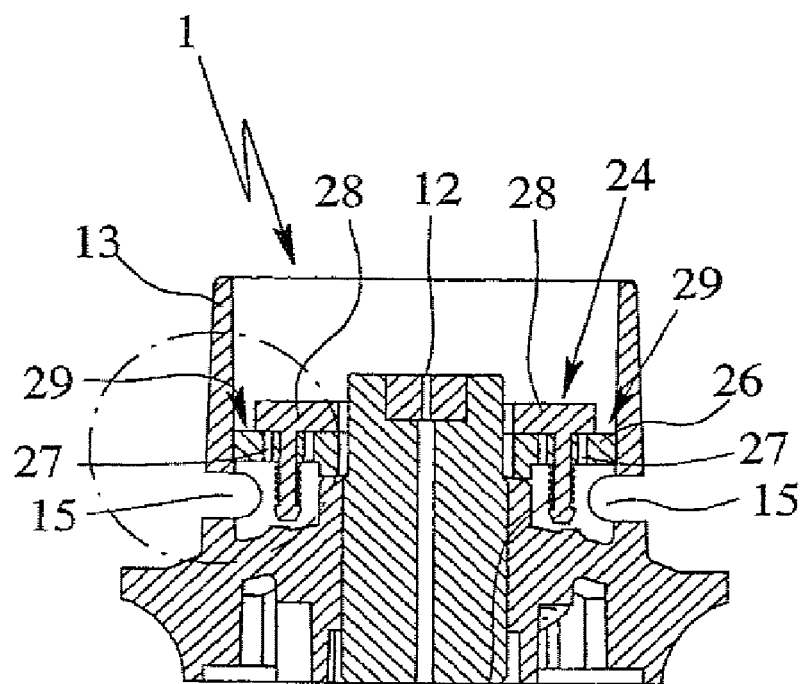
FIG. 3 is a diagrammatic sectional view of a detail of a mouthpiece of a proposed nebulizer according to a first embodiment with a valve device in the closed state.
Figure 4:
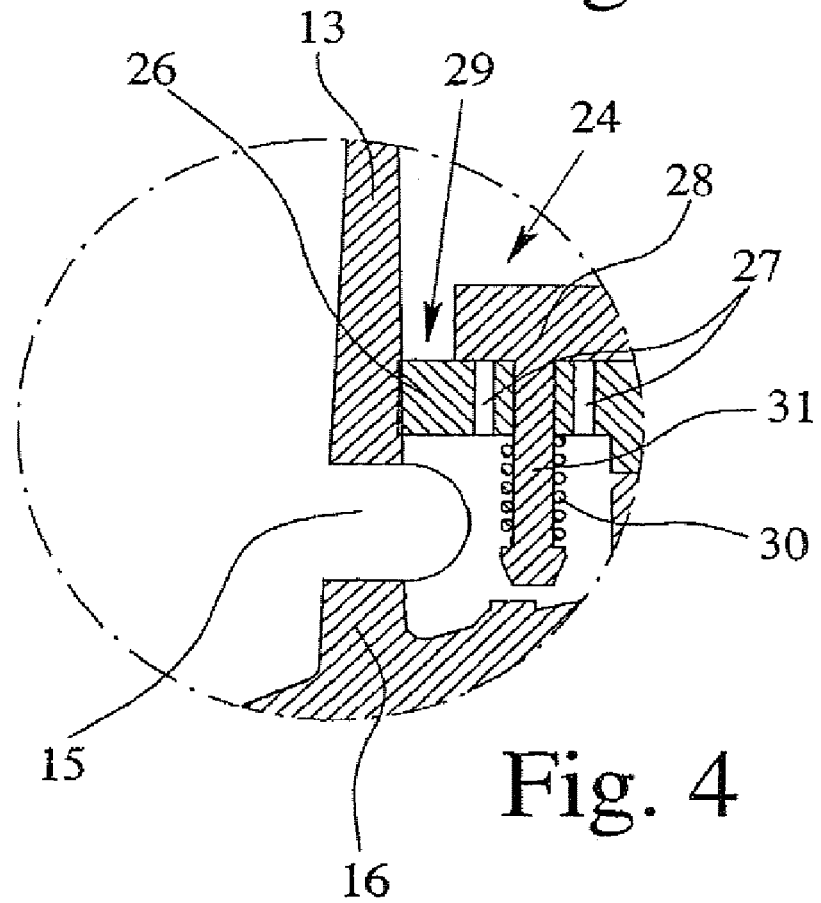
FIG. 4 shows the dot-dash line encircled detail in FIG. 3, shown on a larger scale.
Figure 5:
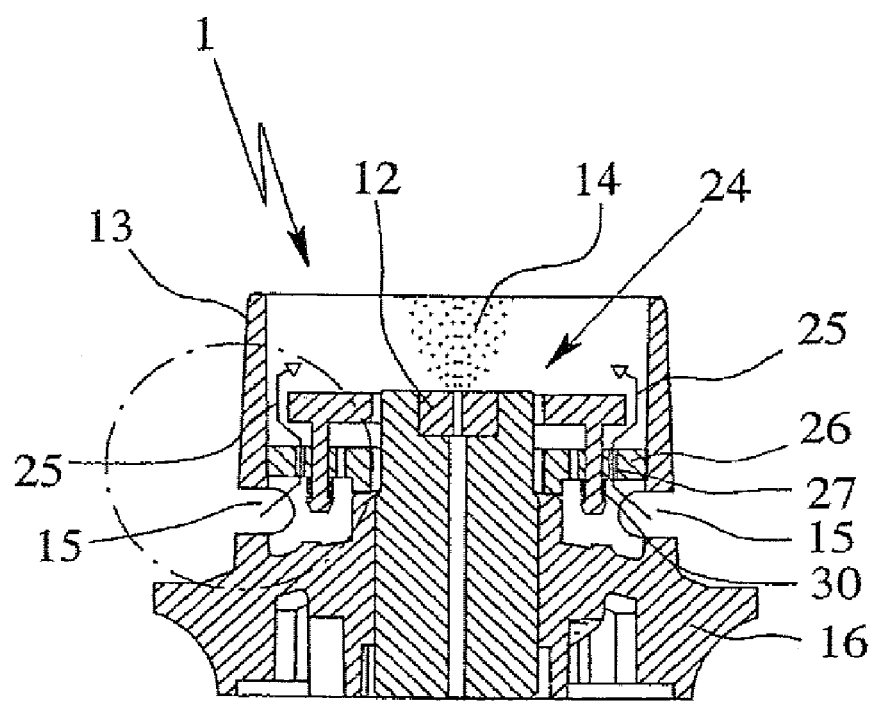
FIG. 5 is a diagrammatic representation of the valve device according to FIG. 3 in the open state.
Figure 6:
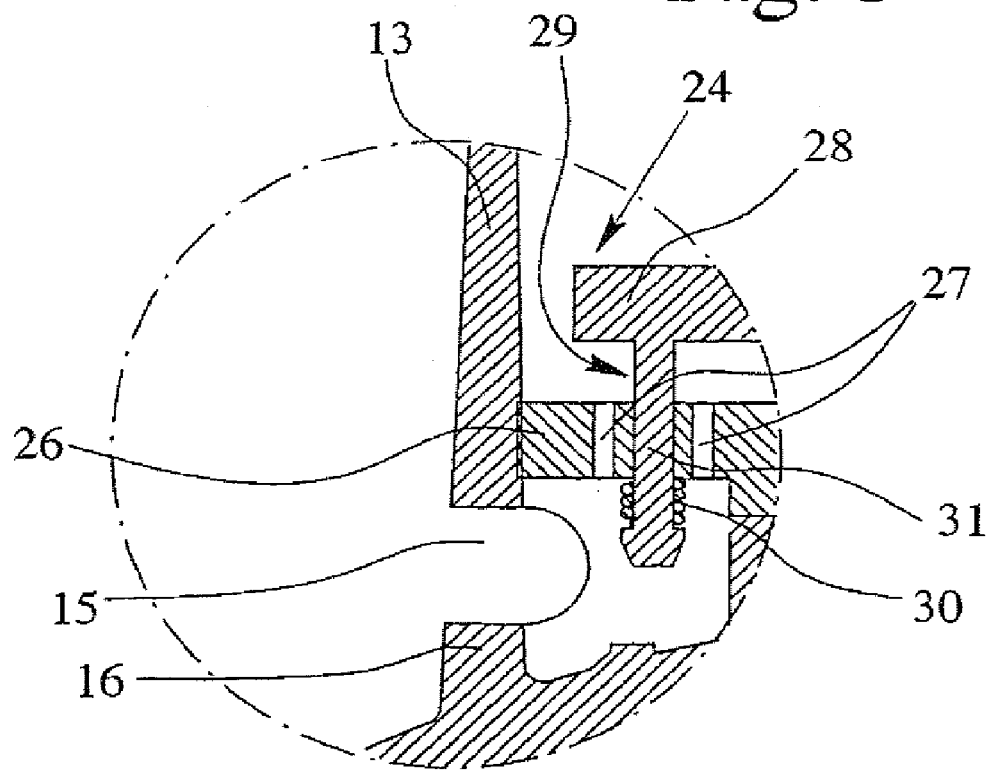
FIG. 6 shows the dot-dash line encircled detail in FIG. 5, shown on a larger scale.

FIGS. 3 to 6 show, in sectional diagrammatic representations of details, a proposed nebulizer 1 having a valve device 24 according to a first embodiment. FIG. 3 shows the valve device 24 in the closed state. FIG. 4 shows the dot-dash line encircled detail in FIG. 3. FIG. 5 shows the valve device 24 in the open state. FIG. 6 shows the dot-dash line encircled detail in from FIG. 5.

In the open state, the valve device 24 allows an air supply current 25, as indicated by corresponding arrow in FIGS. 5 & 6, through the air supply openings 15 into the mouthpiece 13 during inhalation, i.e., breathing in, by a user (not shown) of the nebulizer 1. The user puts the mouthpiece 13 in his mouth and should breathe as evenly and slowly as possible, preferably for several seconds, particularly about 10 seconds or more, thereby inhaling the nebulized fluid 2 or aerosol 14. The air supply is thus breathed in at the same time but is not used to nebulize the fluid 2 or produce the aerosol 14. Rather, this is done separately or independently, preferably without the use of propellant gas, by the pressure generator 5 as explained hereinbefore.

In the embodiment shown, the valve device 24 is arranged in the mouthpiece 13 and preferably alongside the expulsion nozzle 12 for the fluid 2 or aerosol 14. Alternatively, the valve device 24 may be mounted on the outside of the mouthpiece 13 or be associated therewith in some other way. An external arrangement has the advantage that the valve device 24 is not exposed directly to the aerosol cloud in the mouthpiece 13, thereby preventing soiling of the valve device 24.

Preferably, the valve device 24 is inserted into the mouthpiece 13 as a construction unit or assembly, in particular. It can preferably be incorporated afterwards, i.e., as an add-on.

Alternatively, at least one part of the valve device 24 is fixedly mounted, particularly formed, injection molded, glued or similar, to the nebulizer 1, particularly the mouthpiece 13.

According to an alternative embodiment that is not shown in detail, the valve device 24 can be replaced together with the mouthpiece 13. In the embodiment shown, however, the mouthpiece 13 is preferably integrally constructed with the nebulizer 1, especially the upper housing part 16 thereof or is formed thereby.

The valve device 24 is constructed and associated with the air supply openings 15 such that backflow through the air supply openings 15—i.e., an airflow from the mouthpiece 13 through the air supply openings 15 into the atmosphere (counter to the air supply flow 15), which might be produced by the user breathing out, in particular, can be prevented, especially automatically. This ensures that the user breathing out cannot cause the nebulized fluid 2 or aerosol 14 to be undesirably expelled through the air supply openings 15 into the atmosphere. Rather, the valve device 24 preferably ensures that when the mouthpiece 13 is fitted, it is only possible to breathe in through the mouth of the user (not shown) or through the mouthpiece 13, so that there is a greater probability or certainty of the nebulized fluid 2 or aerosol 14 being inhaled by the user. This results in substantially better operational safety.

The valve device 24 is preferably constructed so as to operate at least substantially independently of the spatial orientation of the nebulizer 1.

The valve device 24 may, if necessary, operate by electrical, magnetic, pneumatic or other means. The valve device 24 preferably operates exclusively mechanically, as explained hereinafter with reference to the preferred embodiments.

In the first embodiment, the valve device 24 has a preferably plate-shaped seat element 26 with through-openings 27 and a moveable valve element 28 which is preferably also plate-shaped. The seat element 26 is preferably of one-piece construction and is inserted or incorporated in the mouthpiece 13 such that it seals off the connection to the air supply openings 15 in such a way that air can only flow into the mouthpiece 13 through the through-openings 27.

The moveable valve element 28 is associated with the seat element 26 or through-openings 27 so as to seal off the through-openings 27 in the closed position shown in FIGS. 3 & 4 in order to prevent backflow as described above.

The seat element 26 and the valve element 28, thus, together form at least one valve 29, particularly a non-return valve or one way valve. However, the valve 29 may also be constructed in some other suitable manner.

In the first embodiment, a common seat element 26 and a common valve element 28 are provided for several and more particularly all of the air supply openings 15. However, separate seat elements 26, separate valve elements 28 or valves 29 operating independently may be associated with the air supply openings 15, as will be explained with reference to other embodiments.

In the first embodiment, the valve element 28 is moveable in the longitudinal direction of the nebulizer 1 and/or at least substantially in the direction of the air supply current 25. Furthermore, the valve element 28 is biased into the closed position, particularly by spring force, and in the embodiment shown, by springs 30, preferably helical springs. However, it is also possible to use other suitable springs or biasing means instead of these.

Alternatively or in addition, the valve element 28 may also be biased into the closed position by its own elasticity and/or by gravity.

Moreover, if necessary, the valve element 28 may also be biased into the open position and/or may have two stable positions, on the one hand, the closed position and on the other hand, the open position, in particular.

In the first embodiment, the valve element 28 preferably has bar-like guide elements 31, which are particularly integrally formed thereon, which serve both for moveable guidance and holding of the valve element 28 on the nebulizer 1, particularly on the seat element 26, and also serve to guide or hold the associated springs 30.

The valve device 24 is preferably constructed so that the valve device 24 opens as easily as possible to allow substantially unobstructed inhalation or inspiration. The air supply current 25 is thus as unobstructed as possible. Accordingly, the valve element 28 is preferably easy-acting and the spring force acting in the direction of closing in the first embodiment is as low as possible.

Once the valve device 24 is open—i.e., with the valve element 28 raised as shown in FIGS. 5 & 6—the air supply current 25 can flow at least largely unobstructed through the air supply openings 15 and then through the through-openings 27 into the mouthpiece 13 as the user (not shown) breathes in or inhales.

Some additional embodiments of the proposed nebulizer or the proposed valve device 24 will now be described with reference to the other drawings. In particular, only essential differences from the first embodiment will be described. Otherwise, the same characteristics and benefits apply as in the first embodiment and in the known nebulizer 1.

Figure 7:
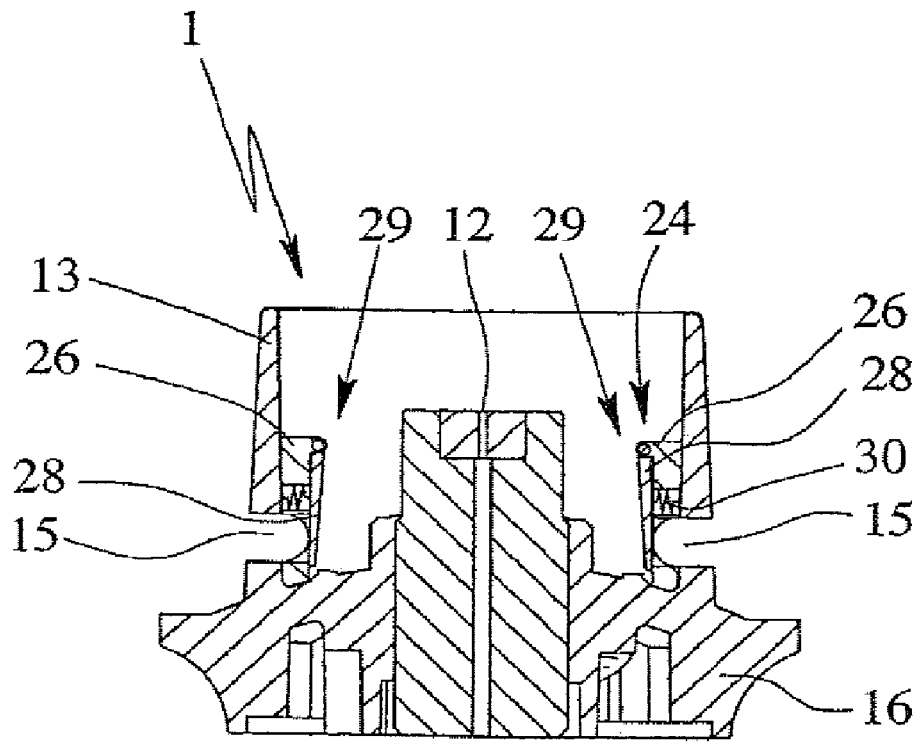
FIG. 7 is a diagrammatic sectional view of a detail of a mouthpiece of a proposed nebulizer according to a second embodiment with a valve device in the closed state.
Figure 8:
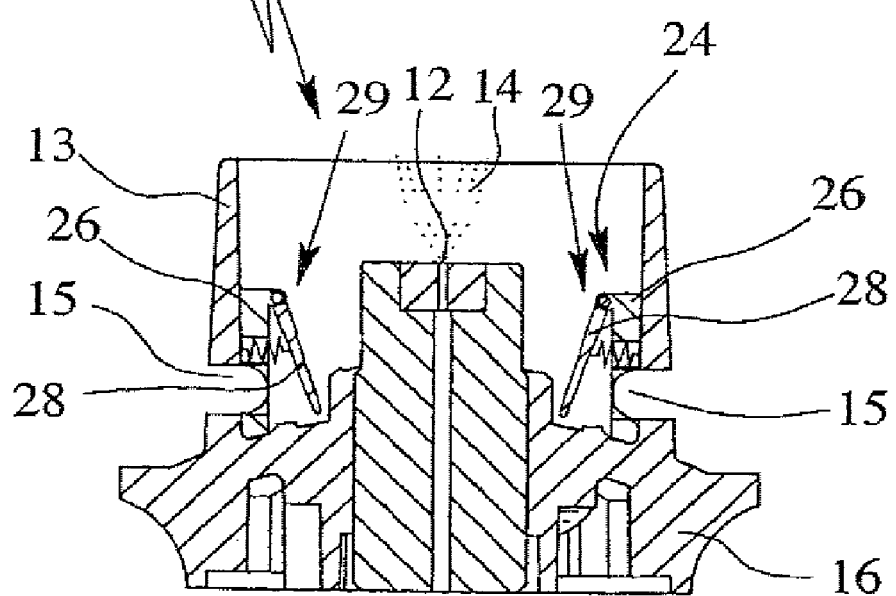
FIG. 8 is a sectional view of the valve device according to FIG. 7 in the open state.

FIGS. 7 & 8 show a second embodiment of the proposed nebulizer 1 and the proposed valve device 24. In FIG. 7, the valve device 24 is closed. In FIG. 8, the valve device 24 is open.

In the second embodiment, separate valve elements 28 or valves 29 are associated with the air supply openings 15. The valve elements 28 are constructed as flaps or tongues and are preferably pivotable. The valve elements 28 preferably cooperate with separate seat elements 26 or directly with the suitably shaped inner wall of the mouthpiece 13, to form the valves 29.

In the second embodiment, the valve elements 28 may if desired be biased into the open position. This allows the user to breathe in or inhale without obstruction. If, however, the user breathes out into the mouthpiece 13, the valve elements 28 are at least substantially instantly closed by the backflow produced, thereby blocking off the backflow. The spring force acting in the open position is selected to be correspondingly low.

Alternatively, however, in the second embodiment, the valve elements 28 may be biased into the closed position as in the first embodiment.

Figure 9:
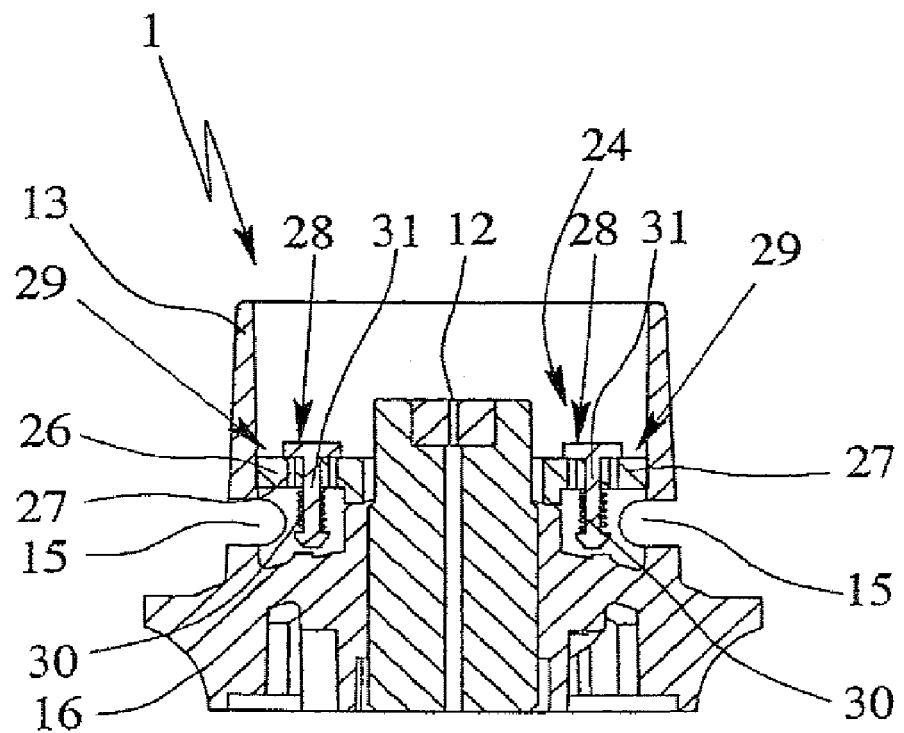
FIG. 9 is a diagrammatic sectional view of a detail of a mouthpiece of a proposed nebulizer according to a third embodiment with a valve device in the closed state.
Figure 10:
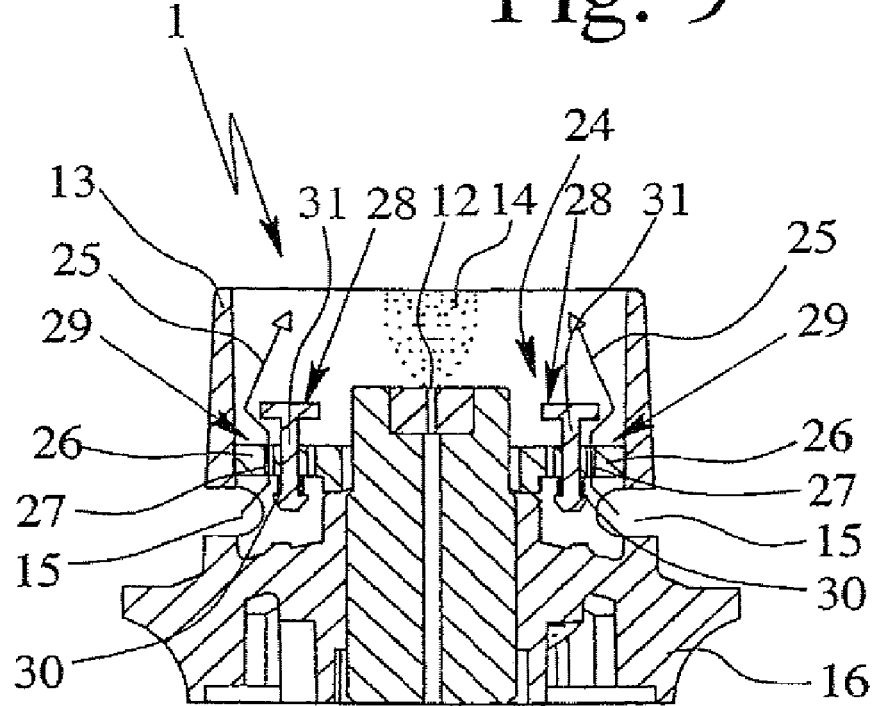
FIG. 10 is a sectional view of the valve device according to FIG. 9 in the open state.
Figure 11:
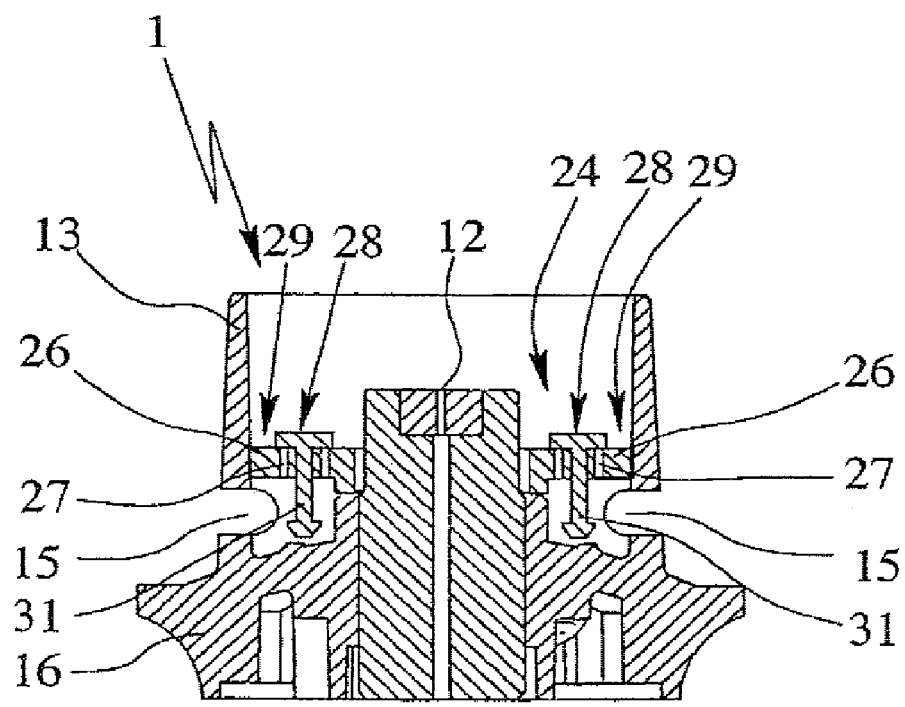
FIG. 11 is a sectional view corresponding to FIG. 9 of a valve device according to a fourth embodiment in the closed state.
Figure 12:
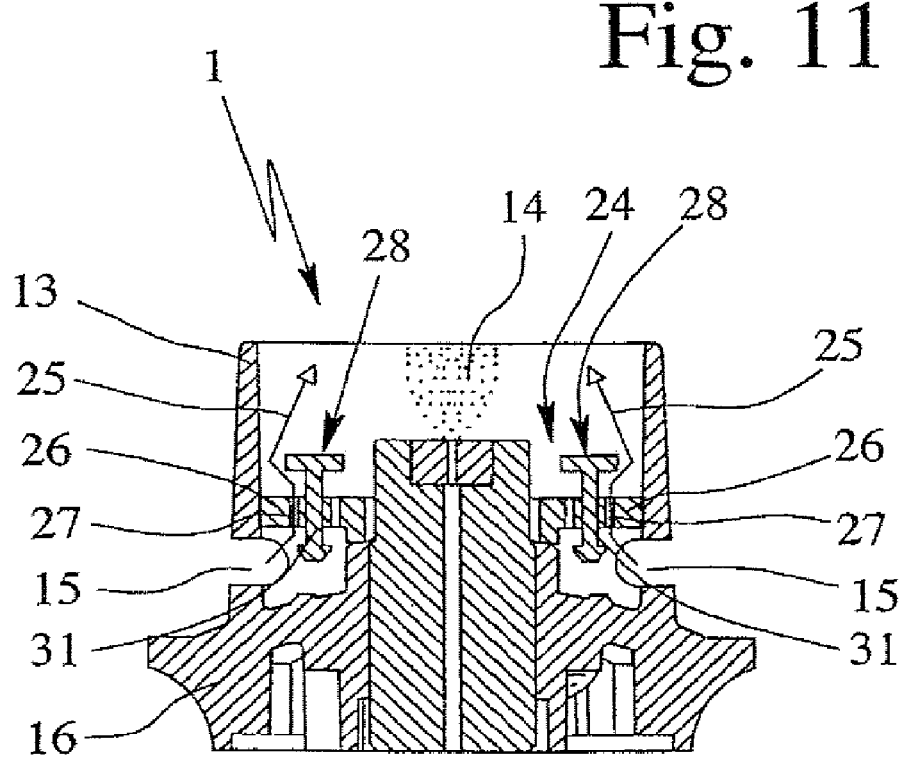
FIG. 12 is a sectional view of the valve device according to FIG. 11 in the open state.
Figure 13:
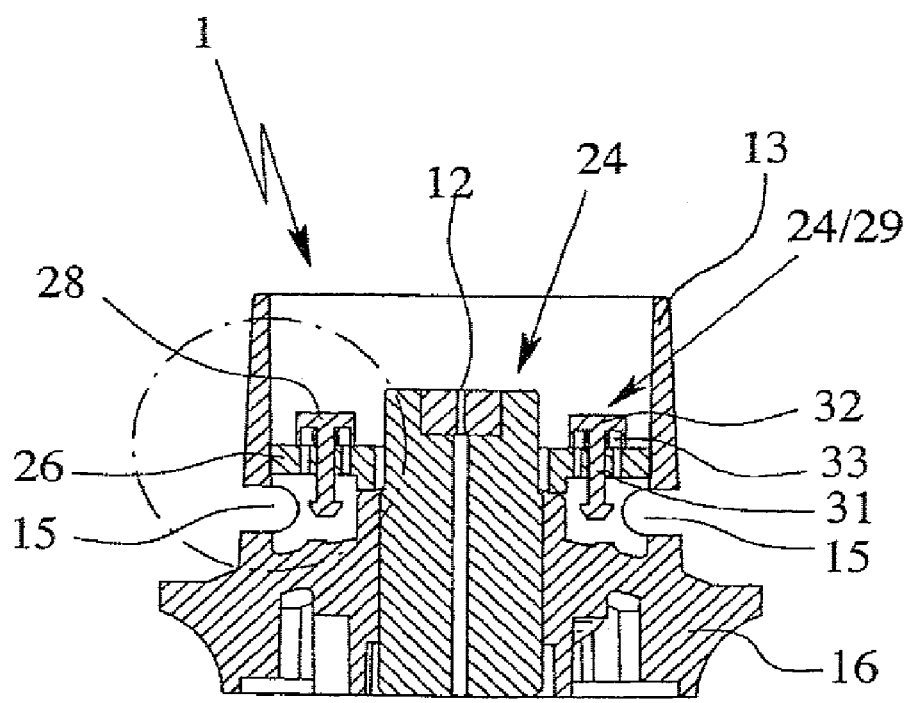
FIG. 13 is a sectional view corresponding to FIG. 9 of a valve device according to a fifth embodiment in the closed state.
Figure 14:
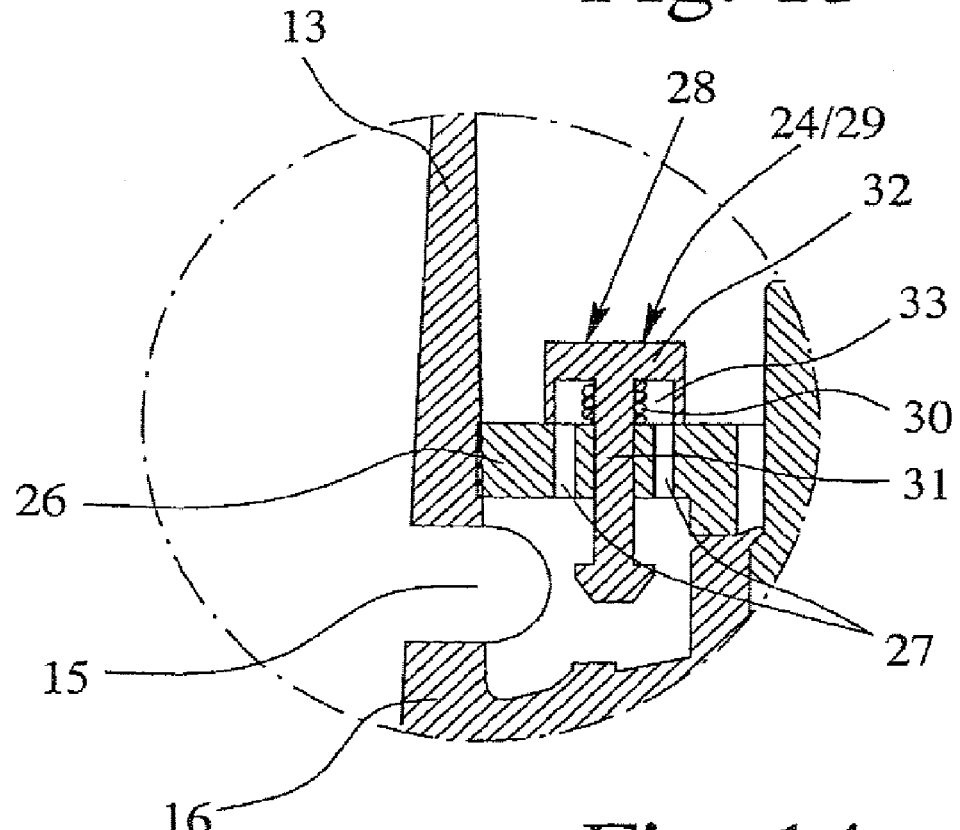
FIG. 14 shows the dot-dash line encircled detail in FIG. 13, shown on a larger scale.
Figure 15:
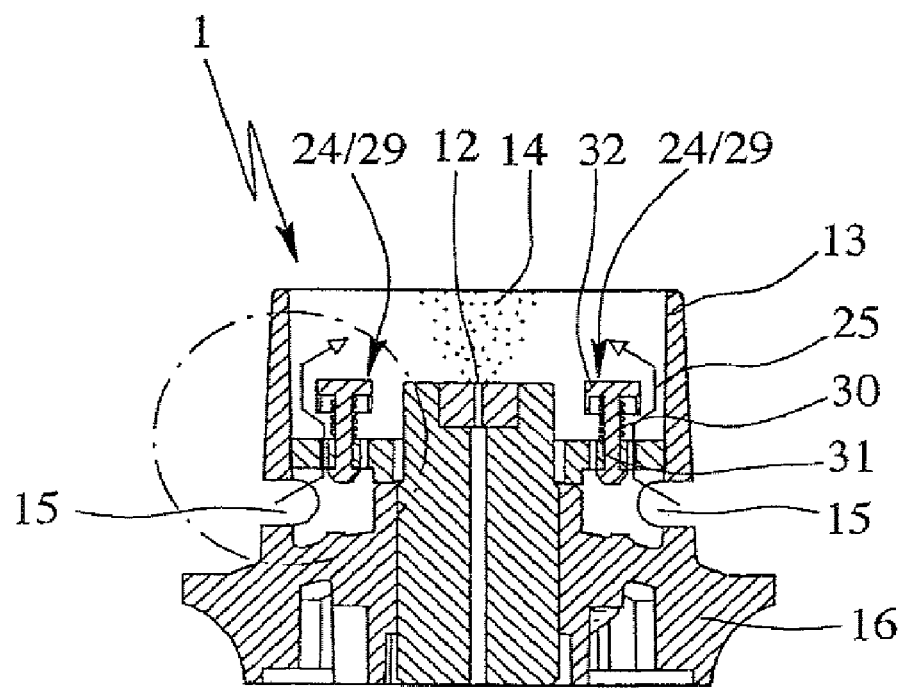
FIG. 15 is a sectional view of the valve device according to FIG. 13 in the open state.
Figure 16:
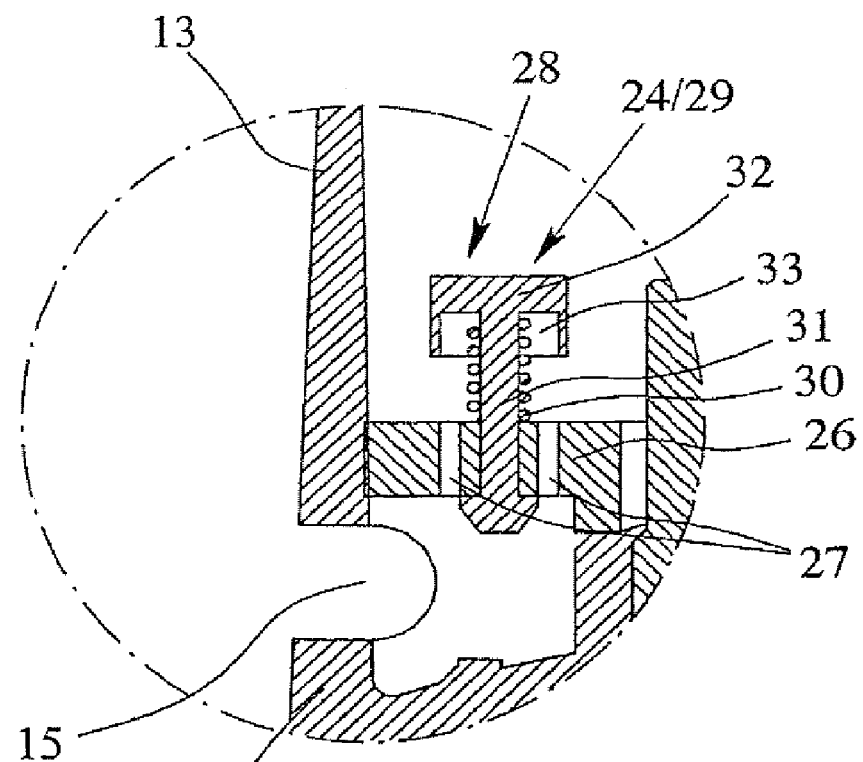
FIG. 16 is a detail from FIG. 15 along the dotted line, shown on a larger scale.
Figure 17:
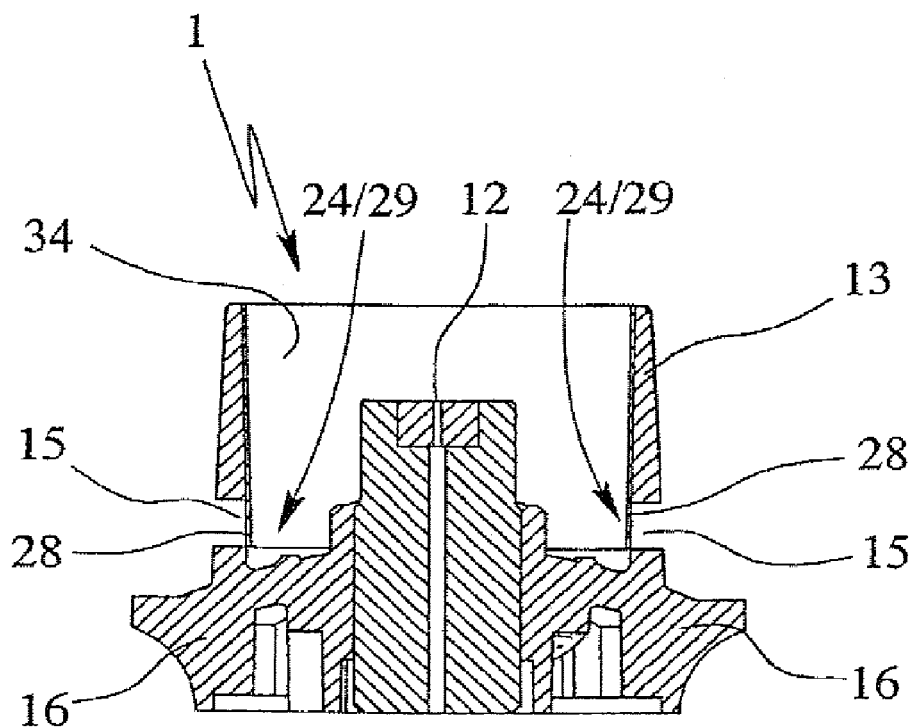
FIG. 17 is a diagrammatic sectional view of a detail of a mouthpiece of a proposed nebulizer according to a sixth embodiment with a valve device in the closed state.
Figure 18:
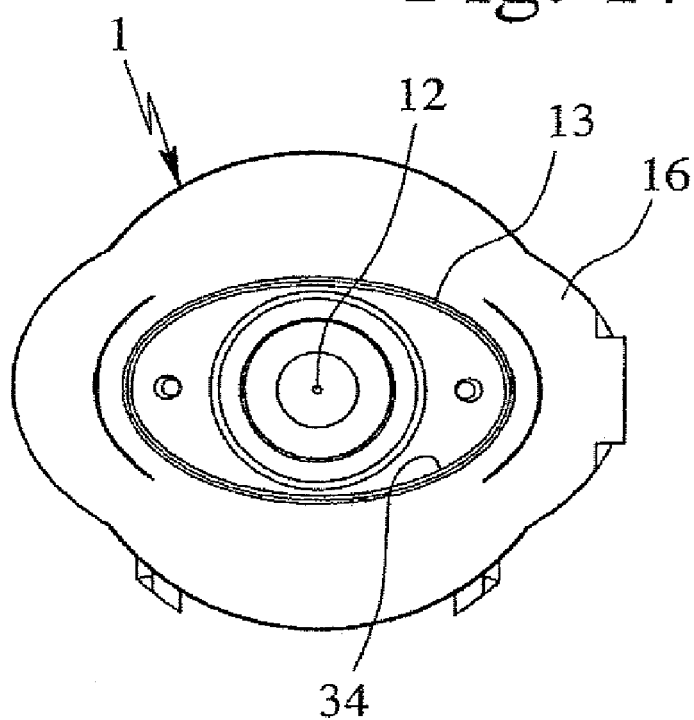
FIG. 18 is a plan view of the nebulizer according to FIG. 17.
Figure 19:
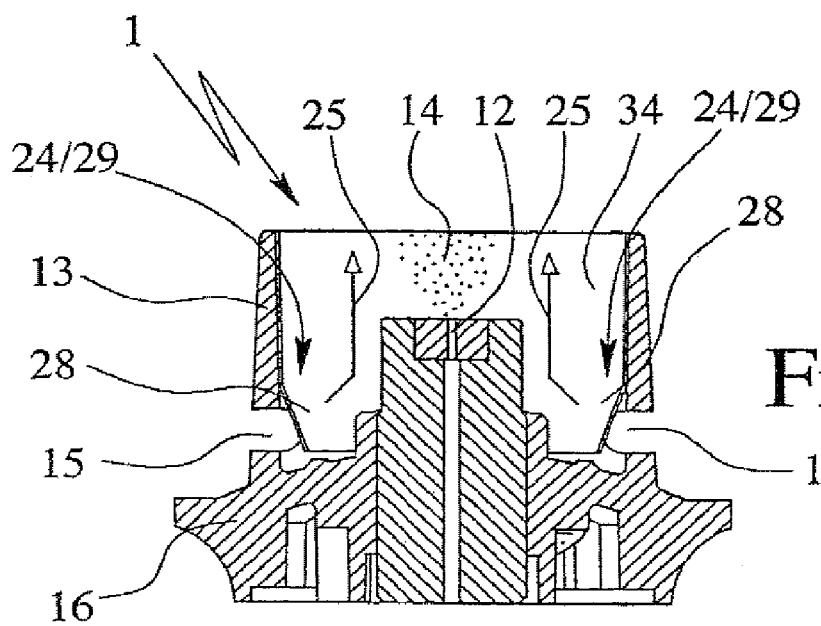
FIG. 19 is a sectional view of the valve device according to FIG. 17 in the open state.
Figure 20:
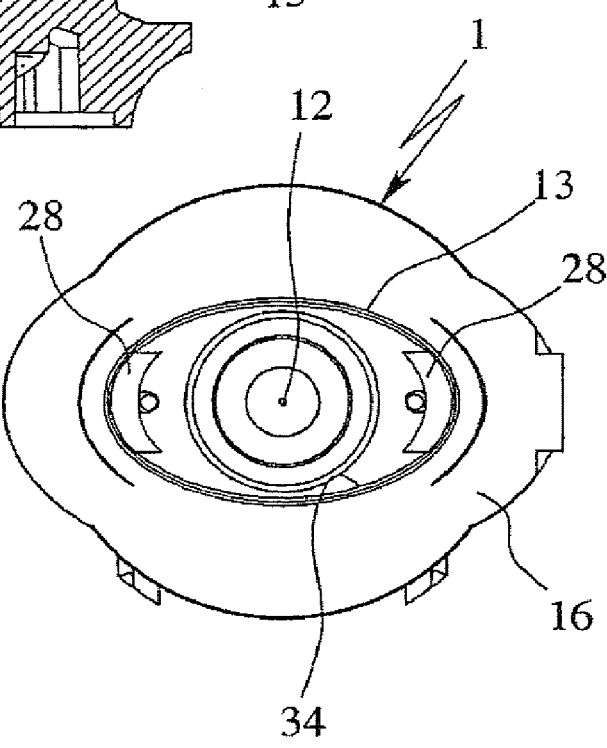
FIG. 20 is a plan view of the nebulizer according to FIG. 19.
Figure 21:
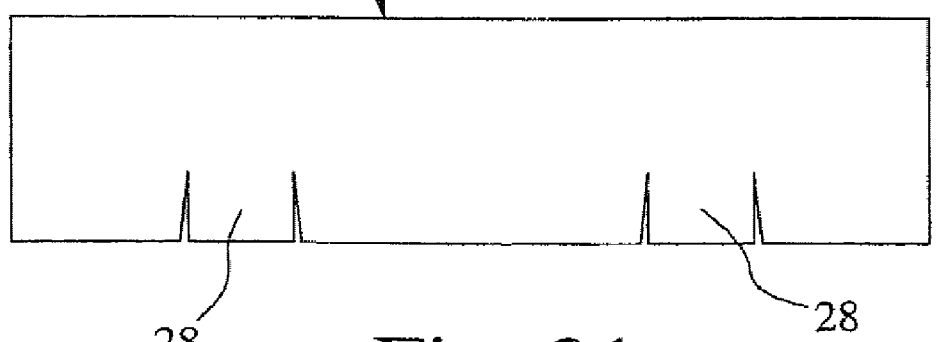
FIG. 21 is a piece of material for forming valve elements of the valve device according to the sixth embodiment.

FIGS. 9 & 10 show a third embodiment of the proposed nebulizer 1 or the proposed valve device 24. FIG. 9 shows the valve device 24 in the closed state. FIG. 10 shows the valve device 24 in the open state.

In the third embodiment, preferably several separate or independently operating valve elements 28 or valves 29 are again provided, and in particular, associated with the air supply openings 15.

As in the second embodiment, the valve elements 28 are also constructed as plates or tappets. Preferably, the valve elements 28 are guided in a common seat element 26 as in the first embodiment.

Again, the valve elements 28 and valves 29 are preferably biased into the closed position by springs 30, particularly helical springs.

In the third embodiment, each valve element 28 preferably comprises a guide element 31 which, in turn, as in the first embodiment, serves, on the one hand, to guide and hold the valve element 28 preferably on the seat element 26, and on the other hand, to guide or hold the associated spring 30.

FIGS. 11 & 12 show a fourth embodiment of the proposed nebulizer 1 or the proposed valve device 24. FIG. 11 shows the valve device 24 in the closed state. FIG. 12 shows the valve device 24 in the open state.

The fourth embodiment substantially corresponds to the third embodiment. Only the springs 30 have been eliminated. The valve elements 28 are thus freely moveable or easily moveable, and in particular, are not biased by spring force. However, in the arrangement shown and on the basis that the nebulizer 1 is aligned at least substantially vertically during use, the valve elements 28 may adopt a preferred position, namely the closed position, as a result of gravity.

FIGS. 13 to 16 show a fifth embodiment of the proposed nebulizer 1 or of the proposed valve device 24. FIG. 13 shows the valve device 24 in the closed state. FIG. 14 shows the dot-dash encircled detail in FIG. 13. FIG. 15 shows the valve device 24 in the open state. FIG. 16 shows the dot-dash encircled detail in FIG. 15.

The fifth embodiment substantially corresponds to the third embodiment except that the spring arrangement has essentially been altered. The springs 30 are preferably formed as helical springs, particularly as compression springs. However, in the fifth embodiment, the springs 30 are arranged on the side of the seat element 26 remote from the air supply openings 15, the plates 32 of the valve elements 28 having a suitable recess 33, which is annular in the embodiment shown, for receiving the associated spring 30. Thus, in the fifth embodiment, the valve elements 28 and valves 29 are preferably biased into the open position. Regarding the arrangement and setting of the spring force, the same remarks apply as in respect of the second embodiment.

FIGS. 17 to 21 show a sixth embodiment of the proposed nebulizer 1 or proposed valve device 24. FIGS. 17 & 18 show the valve device 24 in the closed state. FIGS. 19 & 20 show the valve device 24 in the open state. FIG. 21 shows a piece of material 34 in which the valve elements 28 of the valve device 24 according to the sixth embodiment are formed.

The valve elements 28 are elastic and flexible in construction. Because of their inherent elasticity the preferably tongue- or flap-shaped valve elements 28 of the sixth embodiment assume the closed position as their preferred position, i.e., they close off the air supply openings 15. However, during inhaling or breathing in, the valve elements 28 are moved or pivoted inwards, as shown in FIG. 19 in particular. Thus, the air supply openings 15 are opened up and air can flow into the mouthpiece 13.

The valve elements 28 are preferably formed from the same piece of material 34, particularly a foil or other suitable materials. However, the valve elements 28 may also be formed from separate pieces of material 34.

The plan view in FIG. 18 illustrates the closed state. The valve elements 28 are lying flat, i.e., they are not visible in plan view. On the other hand, in the plan view shown in FIG. 20, the valve elements 28 are shown in the open state and are accordingly flexed or pivoted inwards.

The plan views in FIGS. 18 & 20 show that the valve device 24 or the piece of material 34 can be inserted in the inside of the mouthpiece in an encircling or at least substantially flat position. This allows easy and hence inexpensive assembly, and in particular, allows modification of the nebulizer 1.

According to another alternative embodiment (not shown), the valve device 24 or the valve 29 may be constructed so that the valve element 28 is moveable exclusively by gravity and/or the air supply current 25 or an opposite airflow and as a result the associated air supply openings 15 can be opened up or closed off. For example, the valve element 28 may be constructed for this purpose as a loose sealing element or as a loose washer or gasket which is correspondingly moveably mounted in an air supply channel or the like adjacent to the air supply opening 15 or in the mouthpiece 13. In this way, it is possible, for example, to ensure by means of suitable grids, holders, guides, shoulders, constrictions or the like, that the valve element 28 cannot be moved away from its associates air supply opening 15 at will when the air supply current 25 is breathed in, so that as the user breathes out into the mouthpiece 13 an initial backflow immediately causes the valve element 28 to close the associated air supply opening 15 and thereby block the undesirable backflow.

The embodiments described hereinbefore show various constructional solutions. However, other suitable constructional solutions are possible, and if necessary different valve means 24 may be used instead of valve devices 24 which operate purely mechanically.

An essential aspect of the present invention is the fact that the nebulizing of the fluid 2 or the production of the aerosol 14 takes place independently of the air supply current 25. Instead of the direct expulsion of the aerosol 14 through the expulsion nozzle 12 into the mouthpiece 13, the aerosol 14 may initially be expelled into some other receiving chamber in the nebulizer 1 and then be transported to the actual mouthpiece 13 during inhalation or breathing in by the air supply current 25 and be inhaled through it. Accordingly, the term "mouthpiece" is to be understood more broadly as preferably meaning that it comprises a receiving or collecting chamber for the aerosol 14 produced, to which an air supply can be fed through air supply openings 15 and to which a preferably tubular section is attached which is then actually placed in the user's mouth for inhaling or breathing in.

Figure 22:
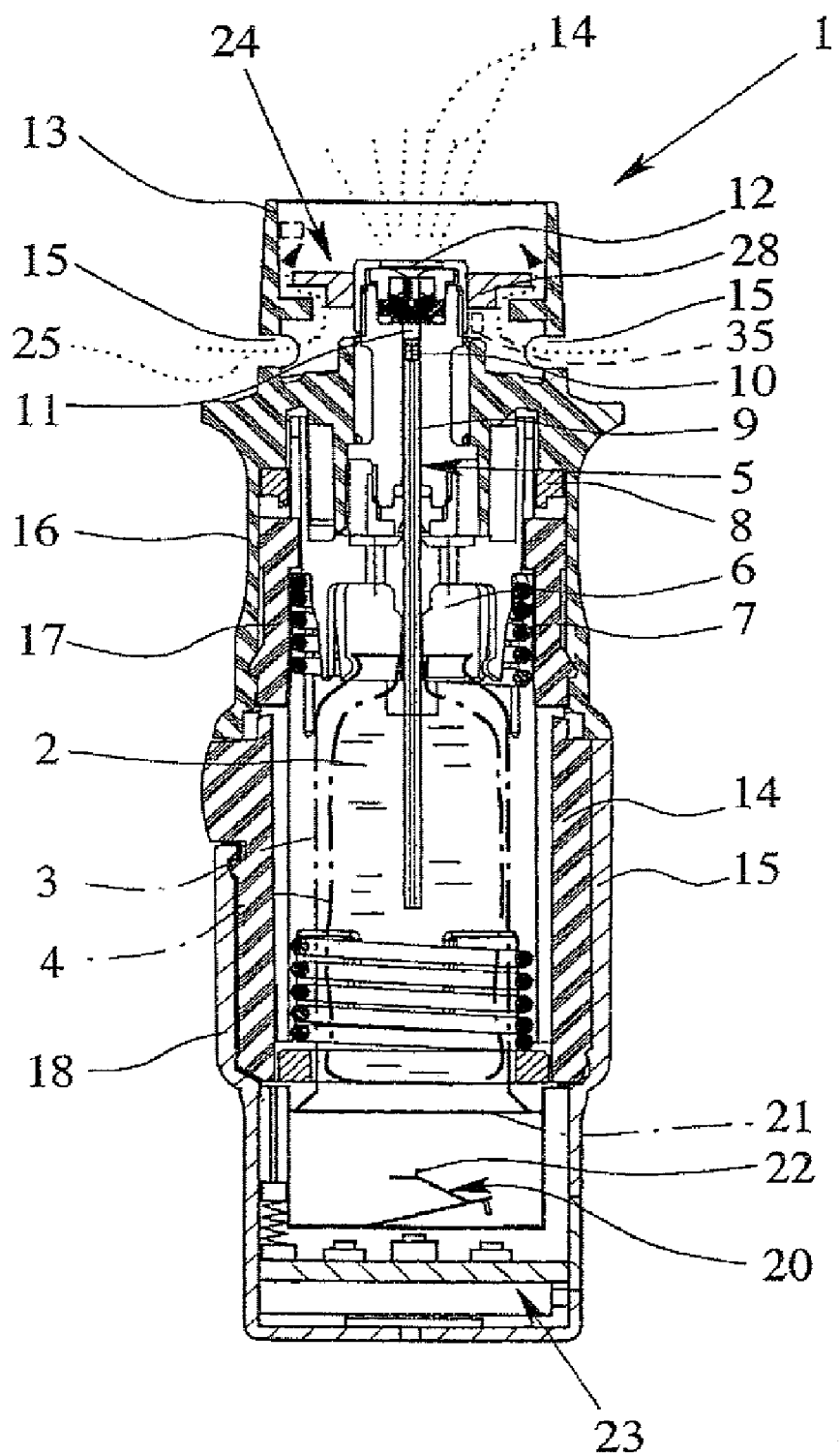
FIG. 22 is a diagrammatic sectional view of a proposed nebulizer according to a seventh embodiment with a valve device in the open state and with an associated sensor.

A preferred feature will now be described in more detail with reference to a seventh embodiment of the proposed nebulizer 1, referring to the diagrammatic sectional view in FIG. 22. This additional feature may, if necessary, be combined, in particular, with the embodiments or valve devices 24 described hereinbefore.

The nebulizer 1 comprises a sensor 35 which is associated with the valve device 24, particularly the moveable valve element 28 or at least one valve 29. The sensor 35 serves to detect the open position, the closed position and/or a movement of the valve device 24, particularly the valve element 28.

The sensor 35 thus also serves to detect movements or at least a position of the valve element 28, and this is done by mechanical, optical, electrical, inductive, capacitive and/or other contactless means. In particular, the sensor 35 is in the form of a microswitch or reed contact.

In the embodiment shown, the sensor 35 is arranged in the immediate vicinity of or adjacent to the valve element 28 and/or in the mouthpiece 13.

By means of the sensor 35, the air supply current 25 is preferably detected indirectly by the opening of the valve device 24, at least the opening of at least one valve element 28 or valve 29. Thus, the actual inhalation of the aerosol 14 produced by the nebulizer 1 can be detected.

Additionally, or alternatively, a so called flow sensor may be provided for directly detecting an airflow and may be arranged, in particular, adjacent to the air supply openings 15.

In the seventh embodiment, the monitoring device 23 is preferably arranged in the housing part 18 and/or constructed so as to be able to detect and evaluate signals from the sensor 35. For this purpose the monitoring device 23 is preferably operated electrically, the sensor 35 preferably being connected to the monitoring device 23 by electrical or wireless means.

The detection by means of the sensor 35 of actual inhalation of the fluid 2 or aerosol 14 can be evaluated by the monitoring device 23 to see whether the inhalation has been sufficiently long, and the inhalation time can, if necessary, be stored and/or displayed. Moreover, this actual inhalation, particularly combined with actual nebulization or a stroke of the container 3 can be detected or counted, displayed and/or stored as the actuation or use of the nebulizer 1.

The monitoring device 23 may, however, also be provided independently of the sensor 35 and may, if necessary, operate mechanically or electrically or electronically, for example.

The proposed nebulizer 1 is preferably constructed to use a liquid as the fluid 2 which is nebulized.

The embodiments described hereinbefore, particularly individual elements and aspects of the embodiments, may if necessary be combined with one another and/or kinematically reversed.

The present invention relates generally speaking to nebulizers 1 for inhalation which generate a virtually stationary cloud of aerosol or a cloud of aerosol with such a low exit speed that the propagation of the cloud of aerosol virtually comes to a stand still after a few centimeters. The exit speed or at least the initial speed of propagation of the cloud of aerosol is preferably about 5 to 20 m/min, particularly 10 to 15 m/min and most preferably about 12.5 m/min.

In particular, because of the low exit speed or speed of propagation the air supply current 25 is needed for taking in the aerosol 14 by inhalation. However, a slight air supply current 25 is preferably sufficient for taking in the aerosol 14 by inhalation.

In order to enable or ensure the desired operation of the nebulizer 1 even at low flow speed and/or flow volumes, the valve device 24 or the valve element 28 thereof or the valve 29 is relatively easy-acting and can be closed with particularly little force. The closing force is preferably only a few cN or less. In particular, the closing force is less than 1 cN, most preferably less than 0.5 cN. The closing force may be produced by gravity alone, inherent elasticity and/or spring bias, particularly from the spring 30, especially in the flap-like construction. In particular, the spring force is preferably only a few cN, particularly not more than 1 cN and most preferably at most 0.5 cN or less.

Figure 23:
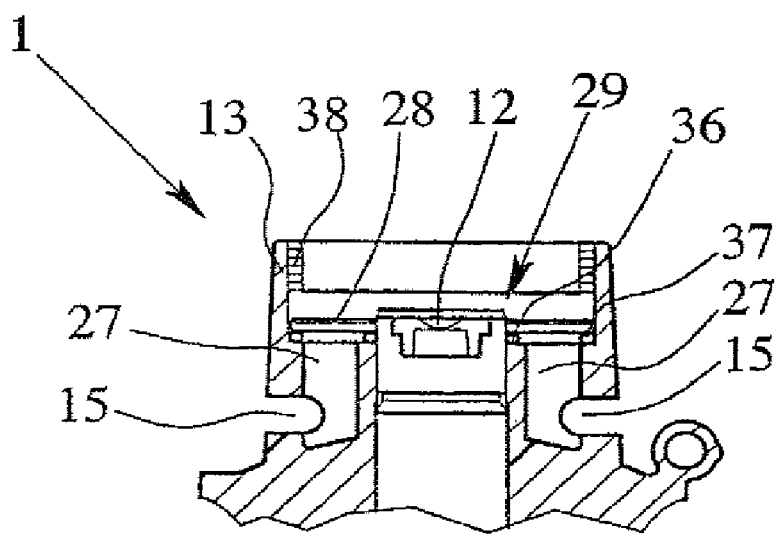
FIG. 23 is a diagrammatic sectional view of a detail of a mouthpiece of a proposed nebulizer according to an eighth embodiment with a valve device in the closed state.
Figure 24:
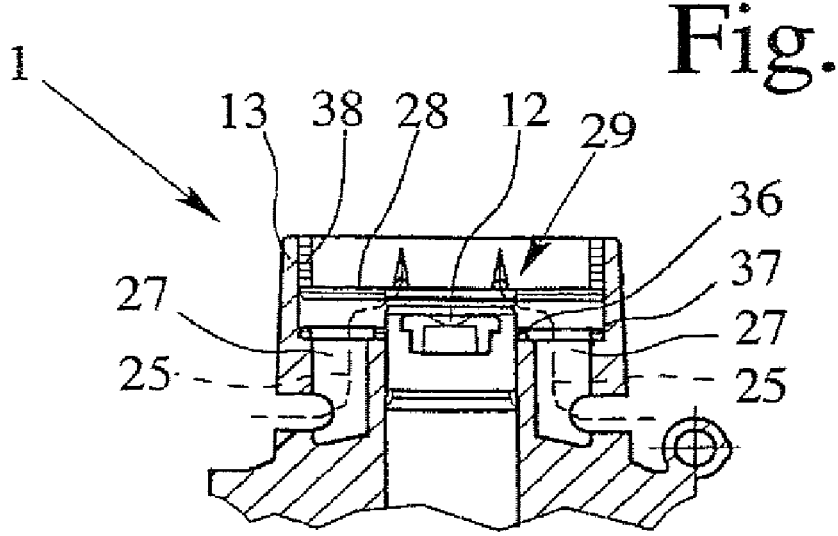
FIG. 24 is a sectional view according to FIG. 23 with the valve device open.
Figure 25:
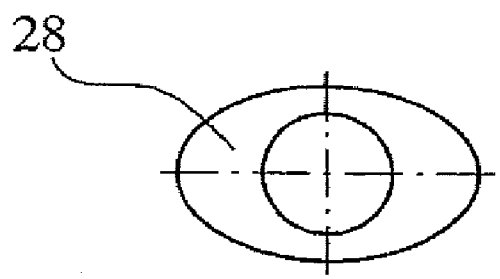
FIG. 25 is a plan view of the valve element of the valve device according to FIG. 23.

FIGS. 23 & 24 additionally shown an eighth embodiment of the proposed nebulizer 1 or the proposed valve device 24. FIG. 23 shows the valve device 24 in the closed state. FIG. 24 shows the valve device 24 in the open state. FIG. 25 is a plan view of the valve element 28 which is plate shaped in this case.

The valve element 28 here is particularly of rigid construction. In the eighth embodiment, the valve element 28 comprises a central recess or opening which is designed so that the central projection with the expulsion nozzle 12 can pass through it, at least when the valve device 24 is closed, as shown in FIG. 23. Thus, the inner contour is designed with the necessary play to fit the projection comprising the expulsion nozzle 12 or other parts of the nebulizer 1 inside the mouthpiece 13.

The outer contour of the valve element 28 is matched to the inner contour of the mouthpiece 13 and in the embodiment shown is elliptical in shape.

Inside the mouthpiece 13, an inner O-ring 36 and an outer O-ring 37, which are arranged concentrically around or below the expulsion nozzle 12 in the embodiment shown form, in particular, a sealing valve seat for the valve element 28 when the valve device 24 is closed. In particular, as a result of its own weight, the valve element 28 bears on the O-rings 36, 37 or other suitable seals to prevent undesirable backflow through the air supply openings 15 (in the closed state).

During inhaling, the valve element 28 is raised by the under pressure, as shown in FIG. 24, as a result of which the valve device 24 or the valve 29 formed by the valve element 28 is opened. The air supply current 25 can then flow into the mouthpiece 13, particularly between the central projection in the embodiment show, which contains the expulsion nozzle 12, and the central recess of the valve element 28.

In the embodiment shown the O-rings 36, 37 are held on suitable annular shoulders, steps or the like in the nebulizer 1 or mouthpiece 13. However, other constructional solutions are also possible, particularly when other suitable seals are used.

In order to limit the play or the stroke of the valve element 28, the nebulizer 1, in the eighth embodiment, preferably, comprises an insert 38 or the like inside the mouthpiece 13, as shown in FIGS. 23 & 24. This insert 38 may, if necessary, be of a circumferential construction and is adapted in particular to the preferably elliptical inner contour of the mouthpiece 13. If necessary, the insert 38 is injection molded, e.g. in the so called 2C process, i.e., in a 2-component injection process. However, other constructional solutions are also possible.

The radial play of the valve element 28 inside the mouthpiece 13 and the mass of the valve element 28 are adapted so that the valve device 24 or valve 29 has the desired easy action. In particular, the remarks made above apply with regard to the closing or opening force.

It should be noted that using the proposed nebulizer 1, an active substance is taken in by inhalation preferably in only one breath. The nebulizer 1 is constructed accordingly. In particular, the nebulizer 1 can generate a sufficiently high droplet or aerosol density and hence active substance density. Precisely in a nebulizer 1 of this kind, the valve device 24 provided for preventing backflow through the air supply openings 15 is particularly important in order to avoid the risk of the entire quantity of active substance being accidentally blown out in the event of the user breathing out.

In contrast to freestanding equipment or the like, the proposed nebulizer 1 is preferably designed to be portable, and in particular, is a hand-held mobile device.

Preferably, the fluid 2 is a liquid, as already mentioned, particularly an aqueous pharmaceutical formulation. However, it may also be a different kind of pharmaceutical formulation, a suspension or the like.

According to one alternative embodiment, the fluid 2 may also be particles or powder. In this case, instead of the expulsion nozzle 12, a different supply device, particularly an expulsion opening (not shown) or a supply channel (not shown) may be provided for supplying the fluid 2 or powder or the like to the mouthpiece 13. The optional air supply opening 15 then serves to supply ambient air, preferably in parallel, so as to generate or permit an air current with sufficient volume for breathing in or inhaling in the mouthpiece 13.

In the previous examples and the above-mentioned alternative embodiment the supply device, particularly the expulsion opening or the expulsion nozzle 12 is constructed to be separate from the air supply opening 15 or any other channel for supplying ambient air. Thus, there is a parallel feed of the fluid 2 or powder or the like, optionally together with conveying gas, propellant gas, transporting air or the like, on the one hand, and ambient air for generating an air current of sufficient volume, on the other hand. However, according to another alternative embodiment, this feed may also take place jointly or together, particularly by means of a common opening (not shown) into the mouthpiece 13. For example, for this purpose, the expulsion nozzle 12 may be integrated in the air supply opening 15 or vice versa.

The valve device 24 in the above-mentioned alternative embodiments may be associated with the air supply opening 15 and/or expulsion opening or the supply channel, so as to avoid undesirable backflow. In particular, in the case of powder or when producing a particle aerosol 14, the valve device 24 is preferably constructed in the form of a clack valve and/or a non-return valve.

It is noted that, if desired, the fluid 2 may also be nebulized using propellant gas. The proposed valve device 24 can be used accordingly in propellant gas-operated nebulizers or inhalers.

It is also noted that the proposed valve device 24 or the mouthpiece 13 fitted therewith may be used not only in the nebulizer 1 specifically described hereinbefore but also in other nebulizers or inhalers, e.g., powder inhalers or so-called metered dose inhalers.

What is claimed is:

1. Nebulizer for a fluid comprising: a mouthpiece, a fluid supply path through which the fluid is supplied to the mouthpiece and at least one air supply opening through which air flows into the mouthpiece, the fluid being sprayed into the mouthpiece separately from and independently of the air flow into the mouthpiece, wherein the at least one air supply opening is associated with at least one valve device by means of which a backflow of air from the mouthpiece back out of the nebulizer is blockable, wherein the valve device ensures that, in the event of a user breathing out into the mouthpiece, an overpressure is produced which indicates a malfunction to the user, wherein inhalation can be continued, as the nebulized fluid or aerosol present in the mouthpiece can continue to be breathed in, and wherein the valve is arranged at least one of in a mouthpiece and laterally alongside an expulsion nozzle for the fluid.

2. Nebulizer according to claim 1, wherein the valve device is insertable as construction unit in the mouthpiece.

3. Nebulizer according to claim 1, wherein at least one component of the valve device is fixedly mounted on the nebulizer.

4. Nebulizer according to claim 1, wherein the valve device is exchangeable together with the mouthpiece.

5. Nebulizer according to claim 1, wherein the valve device operates at least substantially independently of the spatial orientation of the nebulizer.

6. Nebulizer according to claim 1, wherein the valve device operates only mechanically.

7. Nebulizer according to claim 1, wherein the valve device comprises a valve element that is moveable in at least one of a longitudinal direction of the nebulizer and a direction of an air supply current trough the at least one air supply opening.

8. Nebulizer according to claim 1, wherein the valve device comprises at least one of a valve and a moveable valve element.

9. Nebulizer according to claim 8, wherein the at least one air supply opening comprises a plurality of openings all of which are associated with the same valve or valve element.

10. Nebulizer according to claim 8, wherein the at least one air supply opening comprises a plurality of openings, each of which is associated with a separate valve or valve element.

11. Nebulizer according to claim 8, wherein said at least one of a valve and a moveable valve element is a valve element in the form of a plate or flap.

12. Nebulizer according to claim 8, wherein said at least one of a valve and a moveable valve element is a valve element that has an at least substantially rigid construction.

13. Nebulizer according to claim 8, wherein said at least one of a valve and a moveable valve element is a flexible valve element.

14. Nebulizer according to claim 8, wherein said at least one of a valve and a moveable valve element is a valve element that is biased into one of an open and a closed position by at least one of spring force, inherent elasticity and gravity.

15. Nebulizer according to claim 1, wherein the nebulizer comprises a sensor which is associated with the valve device for detecting at least one of opening and closing of the valve device.

16. Nebulizer according to claim 15, wherein the sensor has means for detecting at least one of movements and at least one position of the valve element by at least one of mechanical, optical, electrical, inductive, capacitive and other contactless sensing.

17. Nebulizer according to claim 15, wherein the sensor is a microswitch or reed contact.

18. Nebulizer according to claim 15, wherein the nebulizer has a monitoring device which is adapted to at least one of count and evaluate actuations of the nebulizer and detect whether the sensor has detected at least one of opening and closing of the valve device.

19. Nebulizer according to claim 1, further comprising purely mechanical means for nebulizing of fluid.

20. Nebulizer according to claim 1, further comprising an opening which contains the fluid, and is moveable nebulization.

21. Nebulizer according to claim 1, wherein the nebulizer is constructed as an inhaler for medical aerosol therapy.

22. Nebulizer according to claim 1, wherein the nebulizer is constructed in a manner enabling the fluid to be nebulized independently of an air supply current through the at least one air supply opening.

23. Nebulizer according to claim 1, wherein the nebulizer further comprises a supply device for spraying the fluid into the mouthpiece.

24. Nebulizer according to claim 23, wherein the supply device opens into the mouthpiece separately from the at least one air supply opening and is separate therefrom.

25. Nebulizer according to claim 23, wherein the at least one air supply opening is integrated in the supply device and have a common opening into the mouthpiece.

26. Mouthpiece for an inhaler or a nebulizer, comprising a channel or an air supply opening for supplying ambient air to generate an air current with sufficient volume for breathing in or inhaling, and with a valve device by which backflow through the channel or the air supply opening is prevented, wherein the valve device is a non-return valve.

wherein a supply device for a medium which is to be nebulized opens into the mouthpiece, wherein the supply device opens into the mouthpiece parallel to the channel or the air supply opening, wherein the supply device opens into the mouthpiece separately from and independently of the air current generated by the channel or air supply opening, wherein the valve device ensures that, in the event of a user breathing out into the mouthpiece, an overpressure is produced which indicates a malfunction to the user without preventing continued inhalation of nebulized fluid or aerosol present in the mouthpiece, and wherein the valve is arranged at least one of in a mouthpiece and laterally alongside an expulsion nozzle for the fluid.

27. A nebulizer for a fluid comprising:

a mouthpiece, at least one air supply opening through which air flows into the mouthpiece, a fluid supply path through which the fluid is supplied to the mouthpiece separately from and independently of the air which flows through the at least one air supply opening into the mouthpiece, wherein the at least one air supply opening is associated with at least one valve device by means of which a backflow of air from the mouthpiece back out of the nebulizer is blockable, wherein the valve device ensures that, in the event of a user breathing out into the mouthpiece, an overpressure is produced which indicates a malfunction to the user, wherein the air which flows through the at least one air supply opening is separate from and independent of air use to nebulize the fluid or produce an aerosol, and wherein the valve is arranged at least one of in a mouthpiece and laterally alongside an expulsion nozzle for the fluid.

* * * * *